US006753137B2

(12) United States Patent
Lo et al.

(10) Patent No.: US 6,753,137 B2
(45) Date of Patent: Jun. 22, 2004

(54) CIRCULATING EPSTEIN–BARR VIRUS DNA IN THE SERUM OF PATIENTS WITH GASTRIC CARCINOMA

(75) Inventors: Yuk Ming Dennis Lo, Kowloon (CN); Wing Yee Chan, Tuen Mun (CN); Kwok Wai Ng, Tai Po (CN)

(73) Assignee: The Chinese University of Hong Kong, Shatin (HK)

( * ) Notice: Subject to any disclaimer, the term of this patent is extended or adjusted under 35 U.S.C. 154(b) by 115 days.

(21) Appl. No.: 10/057,579

(22) Filed: Jan. 25, 2002

(65) Prior Publication Data

US 2002/0192642 A1 Dec. 19, 2002

Related U.S. Application Data

(60) Provisional application No. 60/265,568, filed on Jan. 31, 2001.

(51) Int. Cl.[7] .............................. C12Q 1/70; C12Q 1/68
(52) U.S. Cl. ................................................ 435/5; 435/6
(58) Field of Search .......................................... 435/5, 6

(56) References Cited

PUBLICATIONS

Lo et al (Clinical Cancer Research 7: 1856–9, Jul. 2001).*
Anker et al., "Detection of Circulating Tumour DNA in the Blood (Plasma/Serum) of Cancer Patients," Cancer Metastasis Rev. 18:65–73 (1999).
Anker et al.,"K–ras Mutations are Found in DNA Extracted from the Plasma of Patients with Colorectal Cancer," Gastroenterology. 112:1114–1120 (1997).
Chen et al.,"Microsatellite Alterations in Plasma DNA of Small Cell Lung Cancer Patients," Nature Medicine. 2:1033–1035 (1996).
Wong et al., "Detection of Aberrant p16 Methylation in the Plasma and Serum of Liver Cancer Patients," Cancer Res. 59:71–3 (1999).
Mutirangura et al., "Epstein–Barr Viral DNA in Serum of Patients with Nasopharyngeal Carcinoma," Clin Cancer Res. 4:665–9 (1998).
Lei et al., "Quantitative Analysis of Circulating Cell–Free Epstein–Barr Virus (EBV) DNA Levels in Patients with EBV–Associated Lymphoid Malignancies," Br J Haematol. 111:239–46 (2000).
Nawroz et al., Microsatellite Alterations in Serum DNA of Head and Neck Cancer Patients, Nat. Med., 2:1035–1037 (1996).
Lo et al., "Quantitative Analysis of Cell–free Epstein–Barr Virus DNA in Plasma of Patients with Nasopharyngeal Carcinoma," Clin. Cancer Res., 59:1188–1191 (1999).
Capone, "Detection and Quantitation of Human Papillomavirus (HPV) DNA in the Sera of Patients with HPV–Associated Head and Neck Squamous Cell Carcinoma," Clin. Cancer Res., 6:4171–4175 (2000).

Cohen, "Epstein–Barr Virus Infection," N.Engl. J. Med., 343:481–492 (2000).
Drout et al., "High Epstein–Barr Virus Serum Load and Elevated Titers of Anti–ZEBRA Antibodies in Patients with EBV–Harboring Tumor Cells of Hodgkin's Disease," J. Med. Virol., 57:383–389 (1999).
Shibata et al., "Rapid Communication," Am. J. Pathol., 140:769–774 (1992).
Yuen et al., "In Situ Detection of Epstein–Barr Virus in Gastric and Colorectal Adenocarcinomas," Am. J. Surg. Pathol., 18:1158–1163 (1994).
Lo et al., "Quantitative and Temporal Correlation between Circulation Cell–Free Epstein–Barr Virus DNA and Tumor Recurrence in Nasopharyngeal Carcinoma," Cancer Res., 59:5452–5455 (1999).
Gallagher et al., "Detection of Epstein–Barr Virus (EBV) Genomes in the Serum of Patients with EBV–Associated Hodgkin's Disease," Int. J. Cancer, 84:442–448 (1999).
Lo et al., "Molecular Prognostication of Nasopharyngeal Carcinoma by Quantitative Analysis of Circulating Epstein–Barr Virus DNA," Cancer Res., (in press).
Sugawara et al., "Detection of Epstein–Barr Virus (EBV) in Hepatocellular Carcinoma Tissue: A Novel EBV Latency Characterized by the Absence of EBV–Encoded Small RNA Expression," Virology. 256:196–202 (1999).
Yanai et al., "Epstein–Barr Virus–Associated Gastric Carcinoma and Atrophic Gastritis, " J Clin Gastroenterol. 29:39–43 (1999).
Yoshimura et al., Gastric Mucosal Inflammation and Epithelial Cell Turnover are Associated with Gastric Cancer in Patients with Helicobactr Pylori Infection, J Clin Pathol, 53:532–6 (2000).
Hui et al., "Epstein–Barr Virus–Associated Gastric Lymphoma in Hong Kong Chinese," Hum. Pathol., 25:947–952 (1994).
Rogers et al., "Excretion of Deoxyribonucleic Acid by Lymphocytes Stimulated with Phytohemagglutinin or Antigen, " Proc. Natl. Acad. Sci. USA., 69:1685–1689 (1972).
Shotelersuk et al., "Epstein–Barr Virus DNA in Serum/Plasma as a tumor Marker for Nasopharyngeal Cancer," Clin. Cancer Res., 6:1046–1051 (2000).
Lo, Y. et al.,"Kinetics of Plasma Epstein–Barr Virus DNA During Radiation Therapy for Nasopharyngeal Carcinoma," Cancer Res., 60:2351–2355 (2000).
Lo, Y. et al., "Rapid Clearance of Fetal DNA from Maternal Plasma," Am. J. Hum. Genet., 64;218–224 (1999).
Bonnet et al., "Detection of Epstein–Barr Virus in Invasive Breast Cancers," J. Natl. Cancer Inst., 91:1376–1381 (1999).

* cited by examiner

Primary Examiner—Mary E. Mosher (57) ABSTRACT

The present invention features methods for diagnosing, detecting, monitoring and determining the prognosis of gastric cancer, non-head and neck and lymphoid malignancies, and gastritis in a patient by detecting or measuring EBV DNA present in the serum or plasma of the patient. The present invention also features diagnostic kits comprising suitable reagents for detecting EBV DNA in the serum or plasma of a patient.

7 Claims, 4 Drawing Sheets

CIRCULATING EPSTEIN-BARR VIRUS DNA IN THE SERUM OF PATIENTS WITH GASTRIC CARCINOMA

FIELD OF THE INVENTION

This invention relates to the discovery that Epstein Barr virus may be found in the cell free fluid of a patient's blood and when such virus is found and the patient suffers from gastritis, that patient has a predisposition to progress from gastritis to gastric cancer.

BACKGROUND OF THE INVENTION

It is known that tumour-derived DNA can be released by cancer cells of a variety of tumours (Anker et al., Cancer Metastasis Rev. 18: 65–73 (1999)). Examples include onco-gene mutations from pancreatic carcinoma (Anker et al., Gastroenterology. 112: 4–1120 (1997)), microsatellite alterations in lung cancer (Chen et al., Nature Medicine. 2: 3–1035 (1996)) and epigenetic changes from liver cancer (Wong et al., Cancer Res. 59: 3 (1999)). In addition, virus DNA has been found in the circulation of a number of cancers known to be associated with virus infection. Examples include Epstein-Barr virus (EBV) DNA from nasopharyngeal cancer (Mutirangura et al., Clin Cancer Res. 4: 665–9 (1998); Lo et al., Cancer Res. 59: 1188–91 (1999)) and certain lymphomas (Lei et al., Br J Haematol. 111: 239–46 (2000); Gallagher et al., Int J Cancer. 84: 442–8 (1999); Drouet et al., J Med Virol. 57: 383–9 (1999)), and human papillomavirus DNA from head and neck cancer (Capone et al., Clin Cancer Res. 6: 4171–5 (2000)).

Recently, much interest has been focused on the presence of tumor-derived DNA in the plasma and serum of cancer patients (Chen, X. Q. et al., Nat. Med., 2: 1033–1035 (1996); Nawroz, H. et al., Nat. Med., 2: 1035–1037 (1996)). For virally-associated cancers, cell-free tumor-associated viral DNA has been detected in the plasma and serum of patients (Mutirangura, A. et al., Cancer Res., 4: 665–669 (1998); Lo, Y. M. D. et al., Clin. Cancer Res., 59: 1188–1191 (1999); Capone, R. B. Clin. Cancer Res., 6: 4171–4175 (2000)). One important virus which has been associated with many types of malignancy is the Epstein-Barr virus (EBV) (Cohen, J. I. N. Engl. J Med., 343: 481–492 (2000)). Epstein-Barr virus (EBV) is a human herpesvirus that infects the majority of the human population. EBV is commonly transmitted by saliva and established latent infection in B lymphocytes where it persists for the lifetime of the host. In this regard, circulating EBV DNA has been detected in the plasma and serum of patients with nasopharyngeal carcinoma (NPC) (Mutirangura, A. et al., Cancer Res., 4: 665–669 (1998); Lo, Y. M. D. et al., Clin. Cancer Res., 59: 1188–1191 (1999)) and certain lymphoid malignancies (Lei, K. I. et al., Br. J Haematol., 111: 239–246 (2000); Drouet, E. et al., J. Med. Virol., 57:383–389 (1999); Gallagher, A. et al., Int. J. Cancer, 84:442–448 (1999)).

EBV infection has also been reported to be associated with a proportion of gastric carcinomas (Shibata, D. et al., Am. J. Pathol., 140:769–774 (1992)). In Hong Kong, approximately 10% of gastric carcinoma cases have been found to be associated with EBV infection (Yuen, S. T. et al., Am. J. Surg. Pathol., 18:1158–1163 (1994)).

The present invention provides methods for detecting EBV DNA in the sera of patients with gastric carcinoma and correlating the amount of EBV DNA so detected into clinical diagnosis or prognosis.

BRIEF SUMMARY OF THE INVENTION

In a first aspect, the present invention features methods for diagnosing, detecting, monitoring and determining the prognosis of gastric cancer in a patient. The methods feature detecting or determining the amount of Epstein Barr Virus DNA (EBV DNA) present in the serum or plasma of gastric cancer patients. Accordingly, the present invention have broad applicability in clinical medicine.

The methods according to the present invention are also applicable for diagnosing, detecting, monitoring and determining the prognosis of non-head and neck and lymphoid malignancies, such as breast cancer. These neoplasms have been associated with EBV infection as has gastric cancer.

The methods according to the present invention are also applicable for diagnosing, detecting, monitoring and determining the prognosis of gastritis. EBV DNA can be detected in the plasma and serum of patients having non-neoplastic gastric diseases, such as gastritis. In turn, gastritis has been linked to gastric cancer. The invention further comprises patients that can be or have been diagnosed with gastric cancer and the cancer cells are free of EBV nucleic acid or contain EBV.

The methods according to the present invention generally comprise the steps of (1) obtaining a blood sample from a patient, (2) extracting DNA from the blood sample, (3) measuring the amount of circulating EBV DNA present in the blood sample, and (4) comparing the amount of circulating EBV DNA present in the blood sample to a control.

Preferably, the blood sample is a non-cellular fluid sample. By non-cellular we mean that the sample is either blood sera where the cells are extracted by clotting and separation of the cells from the remaining fluid or by inhibiting clotting and centrifuging the fluid fraction (plasma). The EBV DNA is measured from the fluid fraction. When EBV is found in the fluid of a non-cellular sample, it is understood that the infection is active and infected cells releasing EBV.

In a second aspect, the present invention features diagnostic kits comprising suitable reagents for detecting EBV DNA in the serum or plasma of patients. The kits according to the present invention may further comprise one or more of a device for obtaining a blood sample from a patient, a means to separate the EBV DNA from the blood sample and a means to quantify the amount of EBV DNA present in the blood sample. Such kits are useful for diagnosing, detecting, monitoring and determining the prognosis for gastric cancers and gastritis

DETAILED DESCRIPTION OF THE INVENTION

The present invention features methods for diagnosing, detecting, monitoring and determining the prognosis of gastric cancer in a patient. The methods feature detecting or determining the amount of EBV DNA present in the serum of gastric cancer patients. The methods according to the present invention have broad applicability in clinical medicine. Gastric cancer is present in relatively high incidences in many geographical areas including Japan. It is known that a proportion of gastric carcinoma is associated with EBV infection (Shibata et al., *Am J. Pathol.* 140: 769–74 (1992)). A non-invasive blood test according to the present invention represents a significant clinical advance.

Gastritis, or dyspepsia is an inflammation of the gastric mucosa. Gastritis is a group of related disorders that induce inflammatory changes in the gastric mucosa but differ in their clinical features, histolgoic characteristics and causative mechanism. The inflammation, when chronic, is a known indicator of progression to gastric adenocarcinoma.

Gastritis can be acute or chronic. Some people have gastritis after drinking too much alcohol, eating too much, eating spicy food, or smoking. Others develop gastritis after prolonged use of nonsteroidal anti-inflammatory drugs (NSAIDs) or infection with bacteria such as *Escherichia coli*, Salmonella, or *Helicobacter pylori*. Sometimes gastritis develops after major surgery, traumatic injury, bums, or severe infections. Certain diseases, such as pernicious anemia, autoimmune disorders, and chronic bile reflux, can cause gastritis as well. Clinically, the most common symptoms are stomach upset or pain. Belching, abdominal bloating, nausea, vomiting or a feeling of fullness or burning in the stomach are reported by patients. Blood may also be present in vomit or stool if the stomach lining is bleeding.

Gastritis is diagnosed through one or more medical tests including gastroscopy, biopsy, blood tests for anemia and, stool tests for blood. This test checks for the presence of blood in the stool, a sign of gastritis.

Althought gastritis has been associated with EBV infected persons it has never been associated with an increased progression towards gastric cancer. It is an object of this invention to identify gastritis patients with an increased susceptibility to having gastric cancer. The assays of this invention will benefit patients by allowing physicians to focus on those patients who are at greater risk and employing more aggressive anti-gastritis therapies and more frequent endoscopic evaluations.

Clinically, circulating EBV DNA is applicable in diagnosing and monitoring gastric carcinoma patients who have EBER-positive tumors, similar to what has been achieved for nasopharyngeal cancers (Lo, Y. M. D. et al., *Clin. Cancer Res.*, 59:1188–1191 (1999); Lo, Y. M. D. et al., *Cancer Res.*, 59:5452–5455 (1999)) and certain lymphomas (Lei, K. I. et al., *Br. J. Haematol.*, 111:239–246 (2000); Drouet, E. et al., *J. Med. Virol.*, 57:383–389 (1999); Gallagher, A. et al., *Int. J. Cancer*, 84:442–448 (1999)). The recent demonstration of the prognostic significance of circulating EBV DNA in nasopharyngeal cancers (Lo, Y. M. D. et al., *Cancer Res.*, 60:6878–6881) suggests that EBV DNA measurement has prognostic importance for gastric carcinoma.

The methods according to the present invention are also applicable for detecting, monitoring and determining the prognosis of non-head and neck and lymphoid malignancies where those cancers are both associated with EBV. These neoplasms have also been associated with EBV infection (Bonnet et al., J Natl Cancer Inst. 91: 1376–81 (1999)) as have certain liver cancers (Sugawara et al., Virology. 256: 196–202 (1999)).

The methods according to the present invention are also applicable for detecting, monitoring and determining the prognosis of gastritis. EBV DNA can be detected in non-neoplastic gastric diseases, such as gastritis. It is known that certain types of gastritis are associated with EBV infection (Yanai et al., *J Clin Gastroenterol.* 29: 39–43, 1999). Certain types of gastritis predispose patients to intestinal metaplasia which in turn predisposes to gastric carcinoma (Yoshimura et al., *J Clin Pathol.* 53: 532–6, 2000).

Although a percentage of gastritis patients and the gastric epithelium in these patients were found to show the presence of EBV in the only study of 20 patients by Yanai from Japan, the association between the two has never been established. A recent study of over 242 patients with mild to severe chronic gastritis by Hungermann in Germany indicated that EBV infection has a very low prevalence in these patients, and concluded that EBV infection of gastric epithelia cells is not an event in gastric carcinogenesis.

This invention is the discovery that infection of the gastric epithelial tissues by EBV can be identified by a simple blood test. Previously, only infection of lymphoid and other non-epithelial tissues by EBV was found possible to be detected by a similar method. Since epithelial cells are well known to be refractory to EBV infection, this invention demonstrates a totally new concept and opportunity to first identify those gastritis patients infected with EBV and then secondly, to study the possibility that these patients do have an increased susceptibility to having gastric cancer later on. The assays of this invention will benefit patients by allowing physicians to focus on those patients who are at greater risk and employing more aggressive anti-gastritis or anti-viral therapies and more frequent endoscopic evaluations.

Another objective of this invention is focused on patients that are at high risk of contracting EBV infection that may lead to cancer. Such patients include those that have HLA antigens of the types H2, BW46 and B17, proven to have a high tendency to contract EBV infection leading to nasopharyngeal carcinoma. Other patients that are immunocompromised because of diseases such as the human immunodeficiency virus (HIV) or those receiving immunosuppressant medications after organ transplantation are also at high risk. This invention shows that cases of gastric cancer that have EBV DNA inside the tumor cells can be easily detected. Moreover, even cases of gastric cancer that have no EBV DNA inside the tumor cells can also be detected, so long as there is the presence of EBV infected lymphocytes or other cells in the nearby epithelium. In total, about 35% of the gastric cancer cases that exhibit either tumoral EBV DNA positivity or negativity can be detected by this invention. This new concept will be of great help in the monitoring of patients that, as either a direct or indirect result of EBV infection, are at high risk of developing different forms of cancer. Based on this invention, gastric cancer can be added to the list of diseases that need to be under surveillance, besides the lymphomas.

In situations where solid tissue is evaluated for EBV DNA, biopsy specimens are embedded in paraffin and sectioned into 5–$\mu$m thick sections. DNA is extracted with a QIAamp Tissue Kit (Qiagen) using a protocol recommended by the manufacturer. A final elution volume of 50 μl is used for DNA studies.

Any of the conventional DNA amplification or signal amplification methods may be used for detection of EBV DNA. In most instances, it is desirable to amplify the target sequence using any of several nucleic acid amplification procedures which are well known in the art. Specifically, nucleic acid amplification is the enzymatic synthesis of nucleic acid amplicons (copies) which contain a sequence that is complementary to a nucleic acid sequence being amplified. Examples of nucleic acid amplification procedures practiced in the art include the polymerase chain reaction (PCR), strand displacement amplification (SDA), ligase chain reaction (LCR), and transcription-associated amplification (TAA). Nucleic acid amplification is especially beneficial when the amount of target sequence present in a sample is very low. By amplifying the target sequences and detecting the amplicon synthesized, the sensitivity of an assay can be vastly improved, since fewer target sequences are needed at the beginning of the assay to better ensure detection of nucleic acid in the sample belonging to the organism or virus of interest.

Methods of nucleic acid amplification are thoroughly described in the literature. PCR amplification, for instance, is described by Mullis et al. in U.S. Pat. No. 4,683,195 Methods of nucleic acid amplification are thoroughly described in the literature. PCR amplification, for instance, is described by Mullis et al. in U.S. Pat. Nos. 4,683,195, 4,683,202 and 4,800,159, and in *Methods in Enzymology*, 155:335–350 (1987). Examples of SDA can be found in Walker, *PCR Methods and Applications*, 3:25–30 (1993), Walker et al. in *Nucleic Acids Res.*, 20:1691–1996 (1992) and *Proc. Natl. Acad. Sci.*, 89:392–396 (1991). LCR is described in U.S. Pat. Nos. 5,427,930 and 5,686,272. And different TAA formats are provided in publications such as Burg et al. in U.S. Pat. No. 5,437,990; Kacian et al. in U.S. Pat. Nos. 5,399,491 and 5,554,516; and Gingeras et al. in International Application No. PCT/US87/01966 and International Publication No. WO 88/01302, and International Application No. PCT/US88/02108 and International Publication No. WO 88/10315.

Real-time quantitative PCR is a preferred means to monitor EBV DNA and is based on the continuous optical monitoring of the progress of a fluorogenic PCR reaction (Heide et al. *Genome Res.* 6:986–694,1996 and Lo et al. *Am J. Hum. Genet.* 62:768–775, 1998). In this system, in addition to the two amplification primers used in conventional PCR, a dual-labeled fluorogenic hybridization probe is also included (Livak, et al. *PCR Methods Appl.*, 4357–362, 1995). One fluorescent dye serves as a reporter (FAM), and its emission spectrum is quenched by a second fluorescent dye (TAMRA). During the extension phase of PCR, the 5' to 3' exonuclease activity of the Taq DNA polymerase (9) cleaves the reporter from the probe, thus releasing it from the quencher and resulting in an increase in fluorescence emission at 518 nm.

The methods according to the present invention generally comprise the steps of (1) obtaining a blood sample from a patient, (2) extracting DNA from the blood sample, (3) measuring the amount of circulating EBV DNA present in the blood sample, and (4) comparing the amount of circulating EBV DNA present in the blood sample to a control. Preferably, the blood sample is centrifuged, a fluid fraction is obtained, and the EBV DNA is measured from the fluid fraction.

Those of skill in the art will understand that the DNA may be extracted from a blood sample by many means known in the art. One preferred means is using a QIAamp Blood Kit. Also, the amount of circulating EBV DNA may be measured using one of many known or novel protocols. A protocol comprising a real time PCR amplification system is particularly preferred. Standard procedures for comparing the levels of EBV DNA so detected to a control may easily be devised so as to statistically assess the significance of the values obtained.

Those skilled in the art may readily prepare suitable diagnostic criteria based upon the correlation of clinical progression with the amount of circulating EBV DNA present in a sample. However, generally at least about 200 copies, more preferably at least about 500 copies, and still more preferably at least 1000 copies of EBV DNA/ml of serum are present in patients having gastric carcinoma. This cut-off point of 500 copies of EBV DNA per milliliter of serum only apply to those cases which are cancerous at the time of testing and are shown to contain EBV DNA inside the cancer cells. For patients that have gastric cancer with only EBV positive lymphocytic infiltration but without EBV DNA inside their cancer cells, the levels are lower. This lower level of EBV DNA copies per milliliter of serum is also the characteristics of those patients that only have gastritis.

The number of copies of EBV DNA may be measured over time and correlated to disease progression or regression. Thereby, the present invention provides a non-invasive method that allows diagnosis and subsequent monitoring of gastric carcinoma, gastritis and certain other cancers. It should be noted that the cut-off of 500 copies only apply to cases which are already cancerous at the time of testing. For patients with such lymphocytic infiltration, the levels are lower.

In a second aspect, the present invention features diagnostic kits comprising suitable reagents for detecting EBV DNA in the serum or plasma of patients. The kits according to the present invention may further comprise one or more of a device for obtaining a blood sample from a patient, a means to separate the EBV DNA from the blood sample and a means to quantify the amount of EBV DNA present in the blood sample. Such kits are useful for diagnosing, detecting, monitoring and determining the prognosis for gastric cancers, gastritis, and certain other non-head and neck and lymphoid malignancies.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

EXAMPLES

The following examples are provided by way of illustration only and not by way of limitation. Those of skill will readily recognize a variety of noncritical parameters which could be changed or modified to yield essentially similar results.

Example 1

Materials and Methods

Fifty-one patients with gastric carcinoma were recruited with informed consent from the Prince of Wales Hospital, Hong Kong. Blood samples were taken before surgical resection of the tumor. Following operation, sections of the tumor were taken for in-situ hybridization analysis for EBER (small EBV encoded RNA). Blood samples were also taken from 30 individuals with gastritis, without evidence of cancer carcinoma, and 197 apparently healthy control subjects.

DNA Extraction from Plasma Samples

Peripheral blood (5 ml) can be collected from each subject into an EDTA tube for the isolation of plasma. Blood samples are centrifuged at 1600×g, and plasma carefully removed from the EDTA-containing tubes and transferred into plain polypropylene tubes. The samples are stored at −20° C. until further processing. DNA from plasma samples are extracted using a QIAamp Blood Kit (Qiagen, Hilden, Germany) using the blood and body fluid protocol as recommended by the manufacturer (2). Plasma samples (130–800 µl/column) are used for DNA extraction. The exact amount is documented for the calculation of the target DNA concentration. A final elution volume of 50 µl is used from the extraction columns.

Circulating EBV DNA concentrations were measured using a real time quantitative PCR system towards the BamHI-W fragment region of the EBV genome (Lo, Y. M. D. et al., *Cancer Res.*, 59:1188–1191 (1999)). The principles of real time quantitative PCR and reaction set-up procedures were as previously described (Lo, Y. M. D. et al., *Cancer Res.*, 59:1188–1191 (1999)). Data were collected using an ABI Prism 7700 Sequence Detector and were analyzed using the Sequence Detection System software (version 1.6.3) developed by Applied Biosystems. Results were expressed as copies of EBV genomes per milliliter of serum.

All serum DNA samples were also subjected to real time PCR analysis for the (beta-globin gene (Lo, Y. M. D. et al., *Cancer Res.*, 59:1188–1191 (1999)), which gave a positive signal on all tested samples, thus demonstrating the quality of the extracted DNA. Multiple negative water blanks were included in every analysis.

More specifically, two real-time quantitative PCR systems have been developed for EBV DNA detection: (a) one toward the BamHI-W region; and (b) the other toward the EBNA-I region (Baer, et al Nature, 310:207–211, 1984). The BamHI-W system consisted of the amplification primers (SEQ ID NO: 1) W-44F (5'-CCCAACACTCCACCACACC-3') and (SEQ ID NO: 2) W-119R (5'-TCTT AGGAGCTGTCCGAGGG-3') and the dual-labeled fluorescent probe (SEQ ID NO:3) W-67T (5'-FAM)CACACACTACACACACCCAC-CCGTCTC(TAMRA)-3']. The EBNA-1 system consisted of the amplification primers (SEQ ID NO: 4) EBNA-1162F (5'-TCATCATCATCCGGGTCTCC-3') and (SEQ ID NO: 5) EBNA-1229R (5'-CCTACAGGGT-GGAAAAATGGC-3') and the dual-labeled fluorescent probe (SEQ ID NO: 6) EBNA-1186T [5'-(FAM)CGCAGGCCCCCTCCAGGTA-GAA(TAMRA)-3']. The fluorescent probes contained a 3'-blocking phosphate group to prevent probe extension during PCR. Primer/probe combinations were designed using Primer Express software (Perkin-Elmer Corp., Foster City, Calif.). Sequence data for the EBV genome were obtained from the GenBank Sequence Database (accession number V01555). Real-time quantitative PCR for the β-globin gene consisted of primers and probe, as described previously in Lo, et al. *Am J. Hum Genet* 62:768–775, 1998, and was used as a control for the amplifiability of plasma DNA.

Fluorogenic PCR reactions are set up in a reaction volume of 50 µl using components (except for the fluorescent probes and amplification primers) supplied in a TaqMan PCR Core Reagent Kit (Perkin-Elmer Corp.). Fluorescent probes are custom-synthesized by Perkin-Elmer Applied Biosystems. PCR primers were synthesized by Life Technologies, Inc. (Gaithersburg, Md.). Each reaction contained 5 µl of 10×buffer A; 300 nM of each of the amplification primers; 25 nM (for the EBV probes) or 100 nM (for the β-globin probe) of the corresponding fluorescent probe; 4 MM MgCl$_2$; 200 µm each of dATP, dCTP, and dGTP; 400 µM dUTP; 1.25 units of AmpliTaq Gold; and 0.5 unit of AmpErase uracil N-glycosylase.

DNA amplifications are carried out in a 96-well reaction plate format in a Perkin-Elmer Applied Biosystems 7700 Sequence Detector. Each sample are analyzed in duplicate. Multiple negative water blanks were included in every analysis.

A calibration curve is run in parallel and in duplicate with each analysis, using DNA extracted from the EBV-positive cell line Namalwa (American Type Culture Collection CRL-1432; See Klein et al, *Int J. Cancer*, 10:44–57, 1972) as a standard. Namalwa is a diploid cell line that contains two integrated viral genomes/cell. A conversion factor of 6.6 pg of DNA/diploid cell was used for copy number calculation (Saiki et al., Science, 239:487–491, 1988). Concentrations of circulating cell-free EBV DNA were expressed as copies of EBV genome/ml plasma.

An identical thermal profile was used for the EBV BamHI-W and EBNA-I PCR systems. Thermal cycling was initiated with a 2-min incubation at 50° C. for the uracil N-glycosylase to act, followed by an initial denaturation step of 10 min at 95° C., and then 40 cycles of 95° C. for 15 s and 56° C. for 1 min were carried out.

Amplification data collected by the 7700 Sequence Detector and stored in a Macintosh computer (Apple Computer, Cupertino, Calif.) is then analyzed using the Sequence Detection System software developed by Perkin-Elmer Applied Biosystems. The mean quantity of each duplicate is used for further concentration calculation. The plasma concentration of EBV DNA or the β-globin gene (expressed in copies/ml) is calculated using the following equation:

$$C = Q \times \frac{V_{DNA}}{V_{PCR}} \times \frac{1}{V_{ext}}$$

in which C represents the target concentration in plasma (copies/ml), Q represents the target quantity (copies) determined by a sequence detector in a PCR, $V_{DNA}$ represents the total volume of DNA obtained after extraction (typically 50 µl/Qiagen extraction), $V_{PCR}$ represents the volume of DNA solution used for PCR (typically 5 µl, and $V_{ext}$ represents the volume of plasma/serum extracted (typically 0.13–0.80 ml)).

The presence of EBV in tumor cells was assessed by in-situ hybridization on paraffin-embedded tissue sections using a fluorescein-conjugated oligonucleotide probe for EBER (Novocastra, U.K.) as previously described (Hui, P. K. et al., *Hum. Pathol.*, 25:947–952 (1994)).

Results

Figure 1A:
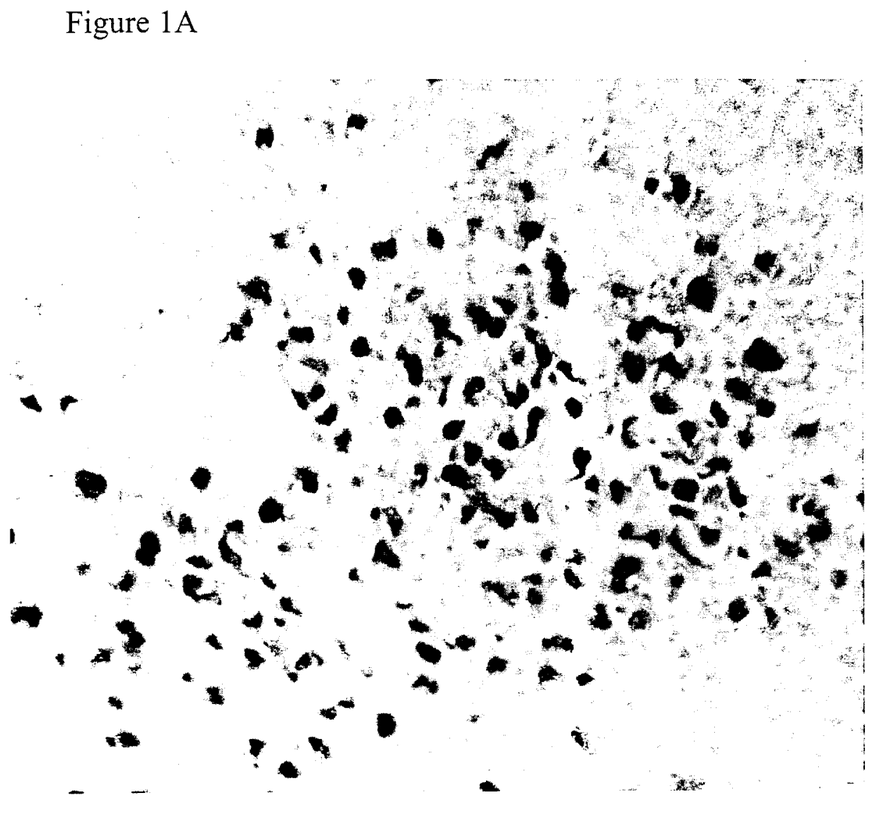
FIG. 1A depicts gastric adenocarcinoma with small EBV encoded RNA (EBER)-positive tumor cells. EBER in-situ hybridization, ×200 magnification.
Figure 1B:
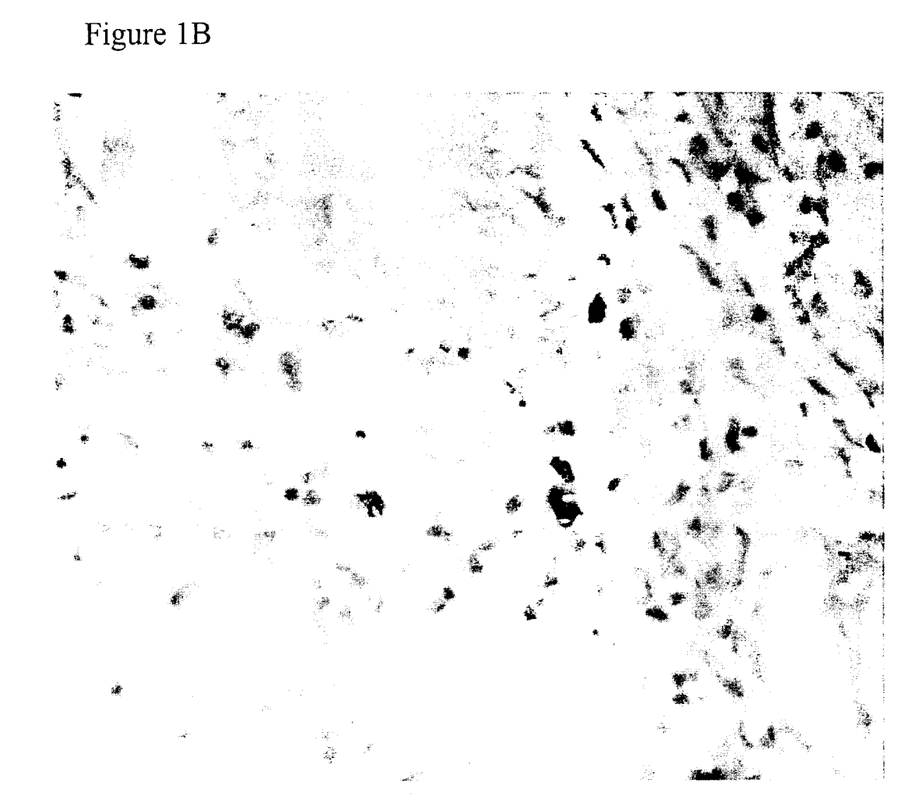
FIG. 1B depicts gastric adenocarcinoma with occasional EBER-positive tumor infiltrating lymphocytes. The tumor cells are negative. EBER in-situ hybridization, ×400 magnification.
Figure 2:
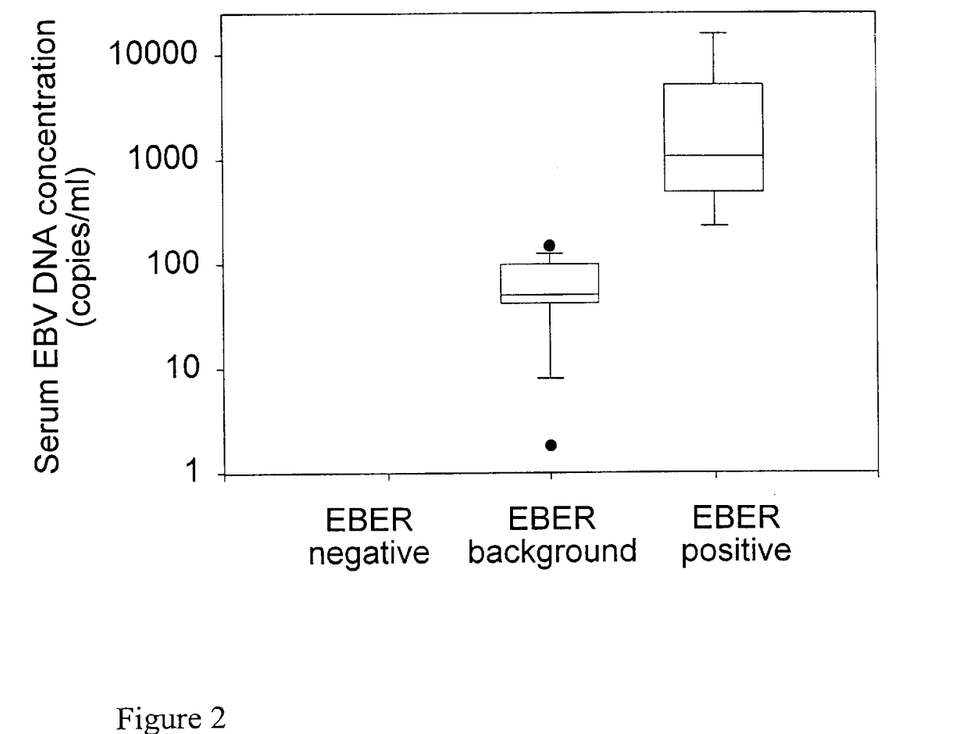
FIG. 2 illustrates the difference in the level of circulating EBV DNA amongst three patient groups. Serum EBV DNA was detected in every one of the EBER-positive cases (median serum EBV DNA concentration: 1063 copies/mL; interquartile range: 485 to 5141 copies/mL). No serum EBV DNA was detected in any of the 32 negative cases. Thirteen out of the 14 cases (93%) demonstrating 'background' EBER positivity had detectable serum EBV DNA. These cases had an intermediate median serum EBV DNA concentration of 50 copies/mL (interquartile range: 42 to 98 copies/mL).

A total of 51 gastric carcinoma patients were recruited. In this cohort, 5 gastric carcinomas were EBER-positive (FIG. 1A). In 14 cases, the tumor cells were EBER-negative, but there were occasional infiltrating lymphocytes which were EBER-positive (FIG. 1B). These 14 cases were classified as having 'background' positivity. FIG. 2 illustrates the difference in the level of circulating EBV DNA amongst these three patient groups. Serum EBV DNA was detected in every one of the EBER-positive cases (median serum EBV DNA concentration: 1063 copies/mL; interquartile range: 485 to 5141 copies/mL). No serum EBV DNA was detected in any of the 32 negative cases (FIG. 2). Thirteen out of the 14 cases (93%) demonstrating 'background' EBER positivity had detectable serum EBV DNA. These cases had an intermediate median serum EBV DNA concentration of 50 copies/mL (interquartile range: 42 to 98 copies/mL). The difference between these three groups is statistically significant (p<0.001, Kruskal-Wallis test). Pairwise multiple comparison analysis indicates significant difference between the EBER-positive and EBER-negative groups (p<0.05, Dunn's method) and between the EBER-background and EBER-negative groups (p<0.05, Dunn's method).

EBV DNA was detectable in the serum of 7 of the 30 gastritis samples (23%) and 7 of the 197 healthy controls (3.6%). The proportions of serum EBV DNA positive cases between these groups are significantly different (chi-square test, p=0.028). Even in the cases with detectable circulating EBV DNA, the actual serum EBV DNA concentrations were generally lower than those in the EBER-positive gastric carcinoma cases.

A comparison was made for the cases with detectable serum EBV DNA in the gastric carcinoma cases with 'background' EBER-positivity, gastritis cases and control subjects. The serum EBV DNA concentrations of these three groups are plotted in FIG. 3. There is no statistically significant difference in circulating EBV DNA levels amongst these three groups (Kruskal-Wallis test, p=0.296).

Discussion

These data demonstrate that cell-free EBV DNA can be detected in serum samples obtained from a proportion of gastric carcinoma patients. In addition, these data demonstrate an interesting correlation between the detectability of serum EBV DNA and tumoral EBER status. Thus, EBER-positive gastric carcinoma cases were associated with high levels of serum EBV DNA; gastric carcinoma cases with 'background' EBER-positivity were associated with intermediate levels; and no serum EBV DNA was seen in EBER-negative cases. This observation lends further demonstrate that plasma and serum represent noninvasive sources of materials for monitoring cancer (Anker, P. et al., Cancer Metastasis Rev., 18:65–73 (1999)).

Clinically, circulating EBV DNA may have application in the diagnosis and monitoring in the proportion of gastric carcinoma patients who have EBER-positive tumors, similar to what has been achieved for NPC (Lo, Y. M. D. et al, Cancer Res., 59:1188–1191 (1999); Lo, Y. M. D. et al., Cancer Res., 59:5452–5455 (1999)) and certain lymphomas (Lei, K. I. et al., Br. J. Haematol., 111:239–246 (2000); Drouet, E, et al., J. Med. Virol., 57:383–389 (1999); Gallagher, A. et al., Int. J. Cancer, 84:442–448 (1999)). Recently, the value of circulating EBV DNA in nasopharyngeal cancer prognosis has been demonstrated. The present data (Lo, Y. M. D. et al., Cancer Res., 60:6878–6881) indicate that EBV DNA measurement also has prognostic importance for gastric carcinoma.

The detection of circulating EBV DNA in gastric carcinomas demonstrating 'background' EBER-positivity is interesting. The EBER-positive lymphocytes infiltrating the tumor tissues may be the origin of the low levels of serum EBV DNA that are detectable in these cases. If this is correct then further work may elucidate the mechanism of EBV liberation by these EBER-positive lymphocytes. Possible mechanisms include active release of DNA (Rogers, J. C. et al., Proc. Natl. Acad. Sci. USA., 69:1685–1689 (1972)) and activation of lytic EBV infection in a proportion of these cells.

Figure 3:
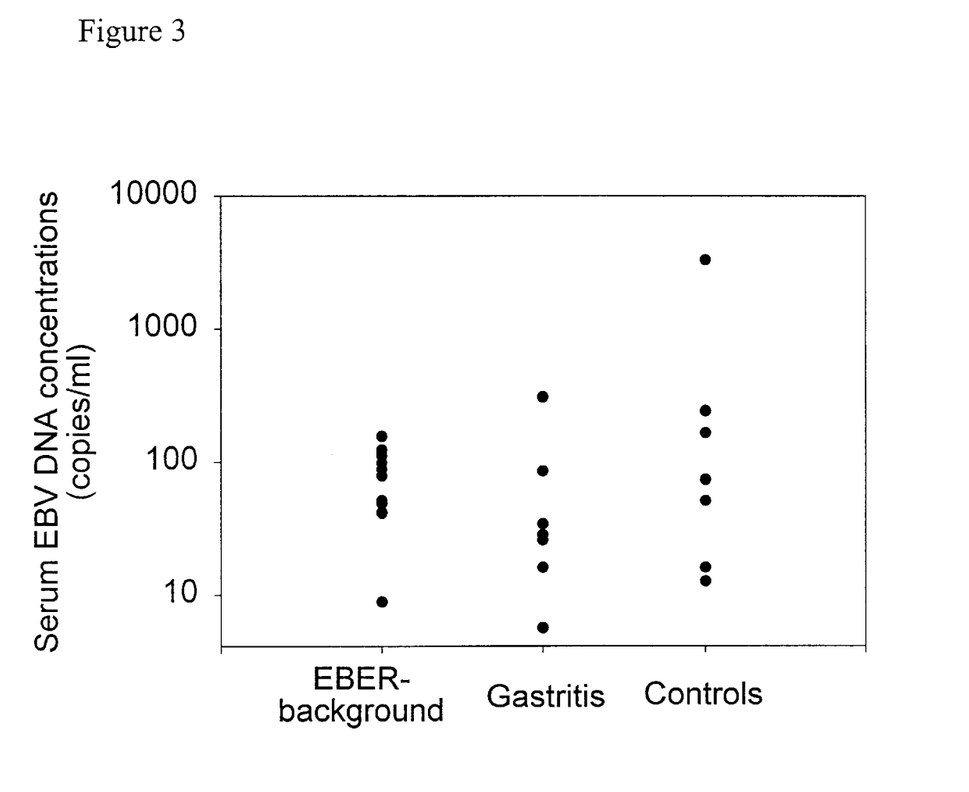
FIG. 3 demonstrates a comparison between cases with detectable serum EBV DNA in the gastric carcinoma cases with 'background' EBER-positivity, gastritis cases and control subjects. The serum EBV DNA concentrations of these three groups are presented. There is no statistically significant difference in circulating EBV DNA levels amongst these three groups (Kruskal-Wallis test, p=0.296).

The association between circulating EBV DNA and EBER-positive infiltrating lymphocytes suggests that low levels of circulating EBV DNA may also be seen in non-neoplastic inflammatory conditions. In fact, circulating EBV DNA is present in gastritis patients. As controls, serum EBV DNA was also detected in 3.6% of apparently healthy control individuals. The presence of low levels of circulating EBV DNA in apparently healthy subjects has previously been reported by other studies (Lo, Y. M. D. et al., Cancer Res., 59:1188–1191 (1999), Shotelersuk, K. et al., Clin. Cancer Res., 6:1046–1051 (2000)). In those gastritis and healthy control cases with detectable serum EBV DNA, the concentrations of viral DNA are very similar to those in the gastric carcinoma cases with 'background' EBER-positivity (FIG. 3). This observation suggests that circulating EBV DNA may also be released by EBV-positive lymphocytes in the gastritis and healthy controls, as has been postulated above for EBER-background gastric carcinoma. With regard to the levels of circulating EBV DNA, amongst these 27 cases with detectable serum EBV DNA, 26 had levels below 500 copies/ml. In contrast, 4 of the 5 (80%) EBER-positive gastric carcinomas and, in a previous study (Lo, Y. M. D. et al., Cancer Res., 59:1188–1191 (1999)), 48 of 57 (84%) of nasopharyngeal carcinoma cases had circulating EBV DNA levels above 500 copies/ml. This analysis suggests that a plasma/serum EBV DNA concentration of 500 copies/ml may be a practical diagnostic cut-off for identifying patients with these carcinomas with high specificity. It is expected that farther refinement of this diagnostic cut-off value will be forthcoming with large-scale clinical studies.

The long-term significance of the presence of low levels of circulating EBV DNA in the blood of apparently healthy individuals remains to be elucidated. Importantly, future studies should address the possibility that these individuals might be at increased risk of developing EBV-associated diseases. This issue would be of tremendous public health and biological importance.

Biologically, the detection of circulating EBV DNA in patients with EBER-positive gastric carcinoma may provide important information regarding the clearance rate of tumor-derived DNA from the plasma. This remains a poorly understood issue because previous work on the kinetics of tumor-derived DNA clearance has been performed in patients undergoing radiation therapy (Lo, Y. M. D. et al., Cancer Res., 60:2351–2355 (2000)) and chemotherapy (Lei, K. I. et al., Br. J. Haematol., 111:239–246 (2000)). The kinetic parameters established from these previous studies represent a composite of (a) tumor cell death due to the treatment regime and (b) the clearance of tumor-derived DNA from the plasma. As gastric carcinoma is treated predominantly by surgical resection, this new model system may provide information regarding the clearance of tumor-derived DNA following cancer removal at a single time point, namely, at surgery. Such information would enhance the understanding of plasma DNA clearance in vivo, just as has already been done for fetal DNA clearance from maternal plasma (Lo, Y. M. D. et al., Am. J. Hum. Genet., 64:218–224 (1999)).

The present data also suggest that circulating EBV DNA may be useful in many other cancer types that are associated with EBV. Examples of such cancers include breast cancer (Bonnet, M. et al., J. Natl. Cancer Inst., 91:1376–1381 (1999)) and hepatocellular carcinoma (Sugawara, Y. et al.,

*Virology*, 256:196–202 (1999)). As the association between some tumor types and EBV is still controversial, the possible detection of EBV DNA in the plasma of patients with such tumors may contribute towards resolving these issues.

What is claimed is:

1. A method of determining whether a gastric carcinoma patient has an EBER-positive tumor by:
   (a) obtaining a sample of non-cellular blood-derived fluid from the patient; and
   (b) assaying the fluid for the presence or absence of Epstein Barr virus DNA; where the presence of the virus DNA in at least about 500 copies/ml is an indication of an EBER-positive tumor.

2. The method of claim 1 comprising the steps of:
   (1) obtaining a blood sample from a patient;
   (2) obtaining a fluid fraction from the blood sample;
   (3) extracting DNA from the fluid fraction; and
   (4) measuring the amount of circulating EBV DNA present in the fluid fraction.

3. The method of claim 2 further comprising the step of:
   (5) comparing the amount of circulating EBV DNA present in the fluid fraction to a control.

4. A method of claim 1 where the blood is a plasma sample.

5. A method of claim 1 wherein the assay involves hybridization of the EBV virus nucleic acid with a nucleic acid probe.

6. A method of claim 1 wherein the assay is a polymerase chain reaction based assay.

7. A method of claim 1 wherein the patient has been diagnosed with chronic gastritis.

* * * * *

```
                         SEQUENCE LISTING

<160> NUMBER OF SEQ ID NOS: 6

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence:BamHI-W
      system amplification primer W-44F

<400> SEQUENCE: 1
cccaacactc caccacacc                                                    19

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:BamHI-W
      system amplification primer W-119R

<400> SEQUENCE: 2
tcttaggagc tgtccgaggg                                                   20

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence:BamHI-W
      system dual-labeled fluorescent probe W-67T
<220> FEATURE:
<221> NAME/KEY: modified_base
<222> LOCATION: (1)
<223> OTHER INFORMATION: n = FAM-labeled c
<220> FEATURE:
<221> NAME/KEY: modified_base
<222> LOCATION: (27)
<223> OTHER INFORMATION: n = TAMRA-labeled c

<400> SEQUENCE: 3
nacacactac acacacccac ccgtctn                                           27

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:EBNA-1
      system amplification primer EBNA-1162F

<400> SEQUENCE: 4
tcatcatcat ccgggtctcc                                                   20

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence:EBNA-1
      system amplification primer EBNA-1229R

<400> SEQUENCE: 5
```

-continued

```
cctacagggt ggaaaaatgg c                                                  21

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence:EBNA-1
      system dual-labeled fluorescent probe EBNA-1186T
<220> FEATURE:
<221> NAME/KEY: modified_base
<222> LOCATION: (1)
<223> OTHER INFORMATION: n = FAM-labeled c
<220> FEATURE:
<221> NAME/KEY: modified_base
<222> LOCATION: (22)
<223> OTHER INFORMATION: n = TAMRA-labeled a

<400> SEQUENCE: 6
ngcaggcccc ctccaggtag an                                                 22
```